United States Patent [19]
Dang et al.

[11] Patent Number: 5,658,263
[45] Date of Patent: Aug. 19, 1997

[54] MULTISEGMENTED GUIDING CATHETER FOR USE IN MEDICAL CATHETER SYSTEMS

[75] Inventors: Ninh H. Dang, Miramar, Fla.; John C. Glasgow, Jr., Earlysville, Va.

[73] Assignee: Cordis Corporation, Miami Lakes, Fla.

[21] Appl. No.: 443,727

[22] Filed: May 18, 1995

[51] Int. Cl.$^6$ .................................................. A61M 25/00
[52] U.S. Cl. ............................ 604/280; 604/282; 604/264
[58] Field of Search .................................. 604/280, 281, 604/282, 283, 264; 138/123, 127, 129, 133, 138, 174; 128/656–658

[56] References Cited

U.S. PATENT DOCUMENTS

| | | |
|---|---|---|
| 3,485,234 | 12/1969 | Stevens . |
| 3,585,707 | 6/1971 | Stevens . |
| 4,563,181 | 1/1986 | Wijayarathna et al. ............. 604/280 |
| 4,596,563 | 6/1986 | Pande . |
| 4,636,346 | 1/1987 | Gold et al. ........................ 604/280 |
| 4,739,768 | 4/1988 | Engelson . |
| 4,753,765 | 6/1988 | Pande . |
| 4,886,506 | 12/1989 | Lovgren et al. . |
| 4,898,591 | 2/1990 | Jang et al. . |
| 4,917,667 | 4/1990 | Jackson . |
| 4,976,690 | 12/1990 | Solar et al. . |
| 5,163,431 | 11/1992 | Griep ............................... 604/282 |
| 5,171,232 | 12/1992 | Castillo et al. . |
| 5,234,416 | 8/1993 | Macaulay et al. . |
| 5,254,107 | 10/1993 | Soltesz ............................. 604/282 |
| 5,279,596 | 1/1994 | Castaneda et al. ................ 604/282 |
| 5,300,048 | 4/1994 | Drewes, Jr. et al. ............... 604/280 |
| 5,308,342 | 5/1994 | Sepetka et al. .................... 604/282 |
| 5,342,386 | 8/1994 | Trotta . |
| 5,387,199 | 2/1995 | Siman et al. ..................... 604/282 |
| 5,403,292 | 4/1995 | Ju ................................... 604/264 |
| 5,441,489 | 8/1995 | Utsumi et al. . |
| 5,445,624 | 8/1995 | Jimenez ........................... 604/280 |

Primary Examiner—Corrine M. McDermott
Assistant Examiner—Ronald K. Stright, Jr.
Attorney, Agent, or Firm—Lockwood, Alex, Fitzgibbon & Cummings

[57] ABSTRACT

The present invention provides a significantly improved guiding catheter for use in catheter systems. It utilizes a segmented body to tailor the catheter strength and flexibility for optimal responsiveness at the distal end. The segmented body utilizes progressively softer materials in the distal direction in order to improve overall maneuverability. The longest and proximalmost segment is substantially straight and harder or stiffer than the rest of the catheter and than typical guiding catheter bodies. This segment performs the function of a handle having a platform at its distal end in order to improve response in the distal segments of the remainder of the catheter. This invention improves the transmission of torque, axial and lateral forces and reduces the likelihood of kinking both laterally and radially. Achieved is improved control of the distal portion through input from the hub at the proximal end of the elongated stiff handle segment. The distal portion provides a softer shaft for transmitting torque over the aortic arch to the tip of the catheter. Guiding is optimized by segment. The softer material portion of the catheter, when inserted, generally coincides with the aortic arch and allows for optimal torque and push force transmission over the arch. Backup support is enhanced, the amount of backup activity being limited more by the ability of the operator to transmit manual input to the tip of the guiding catheter, rather than to tip construction.

16 Claims, 2 Drawing Sheets

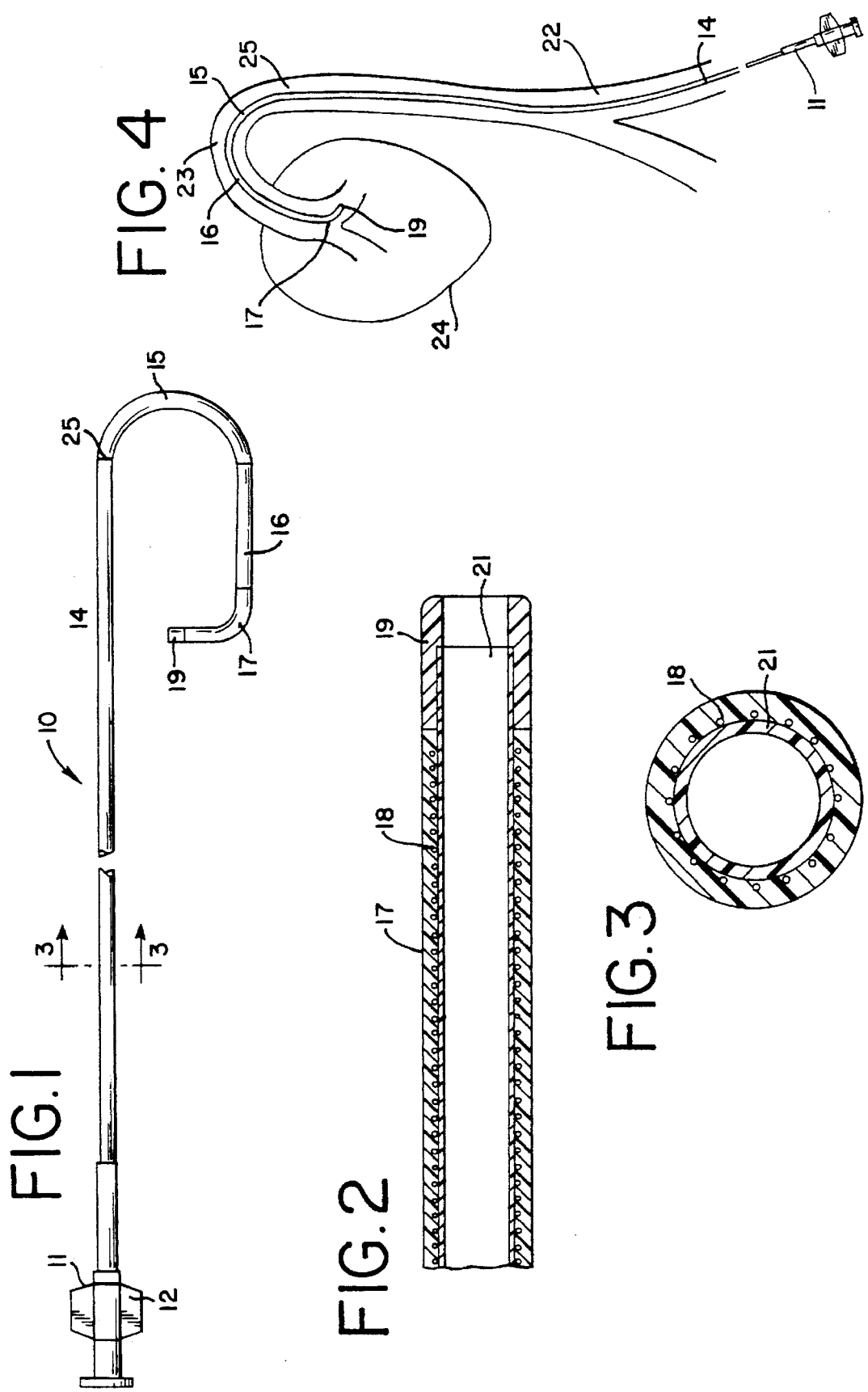

MULTISEGMENTED GUIDING CATHETER FOR USE IN MEDICAL CATHETER SYSTEMS

BACKGROUND OF THE INVENTION

The present invention generally relates to procedures and devices for diagnostic and therapeutic medical procedures requiring use of intravenous catheters, such as those used in cardiac angioplasty. More specifically, the invention relates to guiding catheters such as those suitable for use as a part of catheter systems including those which are used for radiopaque dye injection, for the deployment of laser catheters or other therapeutic devices.

Guiding catheters are used for placing balloon and laser catheters and other medical devices into the desired body vessel, typically a blood vessel such as an artery. Such an artery may be located in or near the heart, brain, abdomen, or peripheral regions. Often, the catheter is inserted into an artery of the arm or leg and threaded to the desired location. The guiding catheter thus becomes the pathway for the other therapeutic or diagnostic medical device.

Since guiding catheters have maneuverability limitations, a guidewire is sometimes inserted first. In these instances, the guiding catheter is inserted over the guidewire. Usually, the guidewire then is withdrawn and the diagnostic or therapeutic catheter introduced through a lumen of the guiding catheter.

Characteristically, the end of the guiding catheter is often formed with a desired curvature to conform to the shape of the location to be treated such as in an artery or to improve maneuverability. The tip is often soft to substantially lessen the risk of trauma to the vessel walls during insertion and/or treatment.

In a typical guiding catheter, the main length, or body, of the guiding catheter is designed for a balance of strength and flexibility. Flexibility improves the ability of the body of the catheter to negotiate the tortuous paths of branching, curving, and narrowing arteries. Those practiced in the art also try to make the body strong by giving it a high torsion modulus and column strength. It has been determined that a strong body reduces the undesirable characteristics called kinking and "whipping" and increases the desirable characteristic called "backup" support.

Catheters sometimes demonstrate "whipping," which is caused by spring torsion. With high spring torsion, the physician experiences a lag in rotational response followed by rotational acceleration. It has been determined that a high torsion modulus reduces the spring torsion and hence the whip. High column strength has been found to improve the ability of the catheter body to withstand lateral forces, axial forces and improve "backup" support. Backup refers to the guiding catheter's ability to provide a reference or backboard for the therapeutic or diagnostic catheter. High column strength also improves the ability of the catheter body to withstanding kinking, and to reduce the angle of kinking when it does occur.

Designs which attempt to balance flexibility with strength generally provide a compromise in performance. Prior approaches designed to improve catheter performance include blending polymers to create desired harnesses (U.S. Pat. No. 4,898,591), multiple layers of polymers (U.S. Pat. No. 4,636,346 and U.S. Pat. No. 4,596,563), and molding polymers over metal braiding (U.S. Pat. No. 4,898,591). Thus, catheters may tend to be designed for maximum rigidity while allowing their minimum acceptable maneuverability. Some prior art has utilized a two segment design which permits better matching of catheter performance for artery location. U.S. Pat. No. 5,342,386 features a more flexible distal segment to improve distal maneuverability in a therapeutic balloon catheter. U.S. Pat. No. 5,171,232 utilizes a braided body and an unbraided transition proximal of the atraumatic tip, giving this therapeutic, diagnostic or guiding catheter greater flexibility in a distal segment.

The present invention is a guiding catheter comprised of several segments which are tailored to meet the maneuverability and firmness needs which vary along the length of a blood vessel. Thus, this invention is firmest at its elongated proximal end portion and most maneuverable at its distal end portion. It is the intent of the invention to have the firm elongated proximal end portion create a firm platform location for the more flexible portion of the catheter at a location which is distally remote and generally coincides with the beginning of a curved or arched area within the vessel. This will provide the greatest controllability at the distal end.

For example, when performing many angioplasty procedures, the guiding catheter is inserted at the leg in the femoral artery about 36 inches (about 90 cm) from the heart artery requiring dilation. Most patients have a substantially straight length of blood vessel, perhaps 29 inches (about 73 cm) in length. This straight length of blood vessel is ideal for a firm catheter body that provides a guiding catheter segment which resembles a "broom handle". In this example, the catheter would then need to maneuver through the aortic arch and perhaps even subsequently smaller vessels with sharper turns. It is not until the aortic arch that the catheter requires considerable flexibility, but the distance from the arch to the coronary arteries is only about 6 to 12 inches (about 15 cm to 30 cm). It is the intent of this invention to design the first or proximalmost segment to be substantially rigid and thus improve the maneuverability of the more flexible distal segments secured thereto.

The firmer catheter segment which extends to an optimum location acts as a relatively long handle that provides more efficient transmission of torque, axial and lateral loads from the hub location to the distal tip location. Thus, with the present invention, the physician experiences improved response when turning the catheter at the tube, when pushing it into the blood vessel and when bending it, all actuated from the hub at the proximal end, as well as when proceeding with diagnostic or treatment catheter backup maneuvers to facilitate passage through a lesion or stenosis.

It is a general object of this invention to provide a catheter more maneuverable and more responsive to the physician's manipulation at the proximal end than are prior guiding catheters.

Another object of this invention is to provide an improved guiding catheter having an in-body platform location therealong in order to provide greater control of more flexible catheter segments distal of this platform location.

Another object of the present invention is to provide an improved guiding catheter having more efficient transmission of torque from the proximal end to the distal end.

Another object of this invention is to provide more efficient transmission of axial loads from the proximal end to the distal end of a guiding catheter.

Another object of this invention is to provide more efficient transmission of lateral loads from the proximal end to the distal end of a guiding catheter.

Another object of the present invention is to provide a firmer guiding catheter surface on which a balloon catheter or the like can be supported when maneuvering it through tight turns or stenoses.

Another object of the present invention is to reduce the likelihood of kinking due to torque, axial or lateral loads applied to a guiding catheter.

Another object of this invention is to reduce the angle of kinking when it does occur during insertion of a guiding catheter.

SUMMARY OF THE INVENTION

The guiding catheter of this invention is generally comprised of a hub at the proximal end, at least three catheter segments which are progressively more flexible in the distal direction, and an atramatic tip at the distal end. It is intended to be inserted through the vascular system or the like and to a location at or near a stenosis or other treatment area. The profile of a guiding catheter according to this invention is substantially the same as other guiding catheters.

The present invention recognizes that improved maneuverability of guiding catheters can decrease the time required to perform an angioplasty or other stenosis treatment procedure, benefitting the physician and the patient. This improvement may be manifested in several ways. Improved maneuverability can decrease the time required to insert the guiding catheter to the desired location. Improved maneuverability may permit the physician to omit the use of a guidewire in some instances. The feature of the invention of a stiff column or "handle" improves the maneuverability of the guiding catheter to the point that a one-to-one type of responsiveness action is approached, if not fully achieved in at least some instances. Time and effort reductions can also be realized in improved maneuverability for the balloon catheter or the like by providing a properly positioned guiding catheter that provides a relatively rigid base for the treatment catheter, especially with respect to improved backup support. These manifestations of improvement all can reduce risk to the patient by potentially shortening the procedure time while also utilizing the physician's time more efficiently. In some instances, the invention may dramatically reduce risk to the patient by eliminating the need for procedures such as coronary bypass surgery because the catheter can negotiate to a stenosis which heretofore may have been unreachable and provide a pathway for the treatment to adequately dilate the artery.

This invention tailors flexibility by utilizing segments of different polymers which vary in hardness. For example, four segments are utilized in the illustrated embodiment, which is suitable for many coronary procedures. Such varying hardness can be conveniently quantified by the Shore hardness system which is used and is widely known by those in the art. The first segment, located at the proximal end, may be likened to a still or rigid handle. It is the hardest segment, preferably having a hardness of about Shore 75 D. The second segment in the distal direction preferably has a hardness of about Shore 64 D. The third segment has a preferable hardness of about Shore 55 D, and the fourth segment has a preferable hardness of about Shore 40 D. The tip is even softer, generally approximately that of a sponge, as will be appreciated to those skilled in the art.

The segments are joined together with a butt weld or other form of heat weld or through the use of an adhesive to form a smooth, continuous assembly. The segments of polymer preferably are molded about a braid of stainless steel or the like. Such braid is commonly used by those skilled in the art to enhance rigidity. It is preferred to line the inside of all segments of the catheter with a lubricious polymer sleeve for facilitating passage of the balloon catheter or other therapeutic device therethrough.

BRIEF DESCRIPTION OF THE DRAWINGS

In the course of this description, reference will be made to the attached drawing, wherein:

FIG. 1 is an elevational view, partially broken away, showing a preferred guiding catheter according to the invention, incorporating a hub, four sections and an atramatic tip;

FIG. 2 shows the distal end of the guiding catheter of FIG. 1 in longitudinal cross-section, including the distalmost section and atramatic tip;

FIG. 3 is an axial cross-section of the guiding catheter of FIG. 1;

FIG. 4 is a somewhat schematic view which demonstrates implementation of the FIG. 1 guiding catheter in a coronary angioplasty or angiography procedure;

DESCRIPTION OF THE PREFERRED EMBODIMENTS

Figure 5:
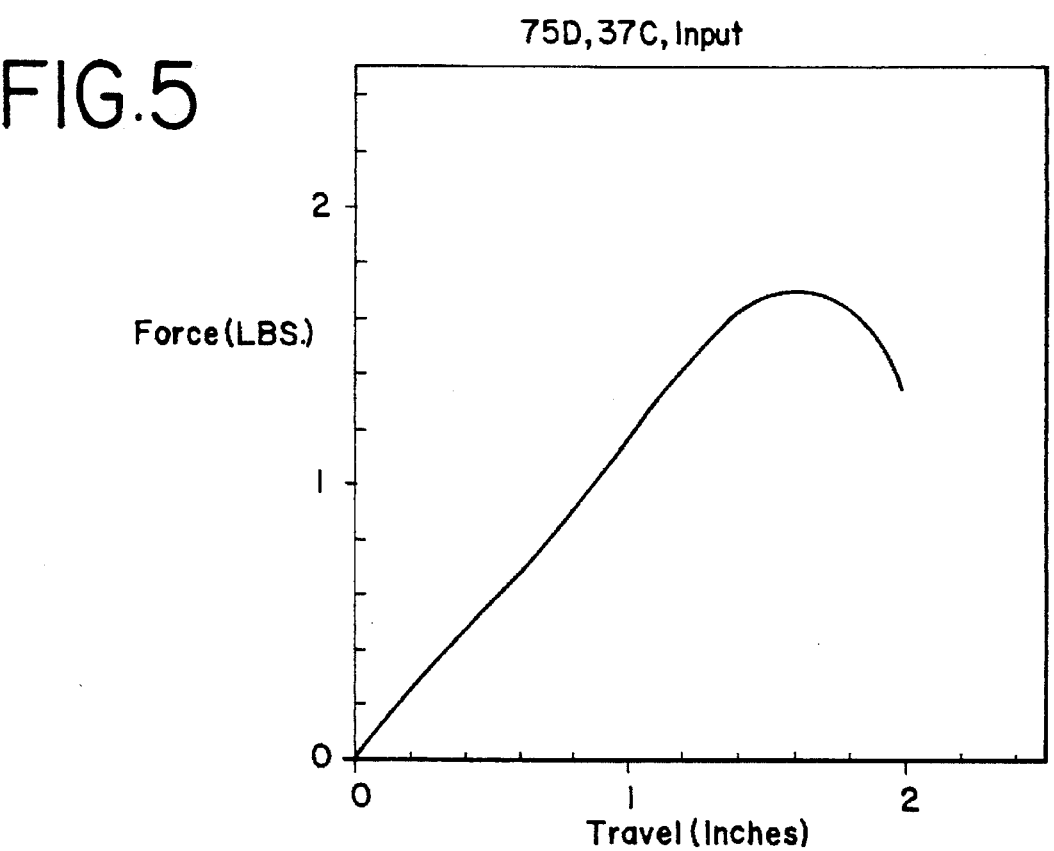
FIG. 5 is a plot of force versus travel illustrating longitudinal rigidity of the proximalmost elongated column shaft according to the invention.

FIG. 1 shows a guiding catheter, generally designated as 10. A hub 11 is positioned on the proximal end of the guiding catheter. The hub 11, in accordance with generally known principles, facilitates connection of guiding catheter 10 to equipment for carrying out desired medical procedures. Also, the hub 11 cooperates with the rest of the guiding catheter in steering the catheter, enabling the physician to easily grasp the distal end of the catheter 10 when guiding it through the arterial branches and to the stenosis. Hub 11 can also serve as a chamfered guide for the balloon catheter. The hub may be of a design similar to those commonly used, allowing for connection to pressurized fluid sources and diagnostic measuring equipment, for example.

Preferably, the hub 11 includes wings 12 which aid maneuverability. A therapeutic or diagnostic catheter or other medical device (not shown) is intended to be inserted into the proximal hole of the hub 11. Hub 11 is sealingly connected to the proximal end of the catheter body and is made of a substantially rigid material, a polycarbonate being an illustrative material.

Distal of the hub 11 is a segmented guiding catheter tube. Typically, it is comprised of at least three segments of progressively softer materials in the distal direction. The proximalmost section is a stiff elongated proximal column tube, while the remaining sections form a modulated-stiffness tube assembly. The embodiment of FIG. 1 shows four segments 14, 15, 16 and 17, and it is a preferable embodiment of the invention and one which is suitable for performing coronary angioplasty.

The first segment 14 is the hardest. It is also the longest segment, being an elongated proximal column tube which extends from the hub to a location which is between about 15 cm and about 30 cm from the distal tip of the catheter. In a typical catheter, this segment 14 extends at least 70 cm, perhaps up to on the order of 90 cm. It preferably possesses a Shore hardness of between about 70 D and about 80 D. A Shore hardness of on the order of about 75 D is preferred. It is intended to be as stiff as possible through the path of the blood vessels when inserted at body temperature. It is stiffer than the body of a typical guiding catheter. Properties as discussed are provided by materials such as nylon or polyamide homopolymers. Especially preferred nylons include Nylon 12. The Nylon 12 can be a homopolymer. Usually this segment, as well as all of the other segments, will be molded about braiding 18, typically of stainless steel.

First segment 14 functions as a stiff column or handle on "top" of which more flexible segments of the catheter rest. An important goal of the invention, through the use of this harder material in the first, elongated proximal column tube segment, is to increase the efficiency of torque transmission, longitudinal load transmission and lateral load transmission for the whole guiding catheter assembly. This segment will also exhibit reduced deleterious effects of kinking by increasing the force necessary to cause kinking and by reducing the kinking angle when it does occur. Enhanced backup support as discussed herein is also achieved.

Turning now to the modulated-stiffness tube assembly, the illustrated embodiment is a three-segment assembly. It is made up of a proximalmost tube section 15 of the modulated-stiffness tube assembly, followed distally by an intermediate tube section 16 and then a distalmost tube section 17.

This proximalmost tube section or segment 15 is intended to be more flexible than the first segment. Segment 15 preferably has a Shore hardness ranging from about 58 D to about 70 D. A Shore hardness of about 64 D is preferred. This second segment 15 is affixed to the harder, column segment 14 by means of a butt weld or other type of heat weld, or by an adhesive or the like. These stiffness properties can be provided by materials such as nylon or polyamide homopolymers having a hardness less than that of the elongated proximal column tube 14. Especially preferred nylons include Nylon 12. The nylon can be a Nylon 12 homopolymer. This polymer would have hardness properties different from those of tube 14, although both could be of the same type of polymer or nylon.

Intermediate tube section 16, when included, is more flexible than the second or proximalmost tube section 15. It has a Shore hardness ranging between about 45 D and about 65 D, preferably about 55 D. Assembly to its adjoining segments is by means of a heat weld, an adhesive, or the like. Stiffness properties within this range are preferably provided by a polymer blend of a stiffer homopolymer and a softer copolymer. Especially useful are blends of polyamide homopolymer and polyamide-containing copolymer. The blend can be of a nylon homopolymer and a nylon copolymer. Preferred is a blend of Nylon 12 (such as one having a Shore hardness of 64 D) with a polyether block amide copolymer, for example a PEBAX (such as one having a Shore hardness of 40 D).

A fourth or distalmost tube section 17 of the modulated-stiffness tube assembly is typically provided. It is secured by heat welding or adhesive means to an adjacent section of the catheter. It is again more flexible than all of the segments positioned proximal thereto. This section 17 has a Shore hardness ranging between about 30 D and about 50 D, preferably about 40 D. This section, as well as any of the other sections of the modulated-stiffness assembly, can be preformed to the shape of the artery section within which insertion is intended so that, once that location is reached, the curve will manifest itself in manner generally shown in FIG. 4. This segment 17 will exhibit these properties when made of a polyamide-containing copolymer such as a PEBAX type of polymer discussed herein. It can be a nylon copolymer.

In a preferred arrangement, the proximalmost tube section can be a nylon homopolymer, the distalmost tube section being a nylon copolymer, and the intermediate tube section being a blend of a nylon homopolymer and a nylon copolymer. Also, the modulated-stiffness tube can have a construction wherein the proximalmost segment 15 is a nylon homopolymer, the distalmost segment 17 is a nylon-containing copolymer, and the intermediate segment 16 is a blend of a nylon homopolymer and a nylon-containing copolymer.

At the distal end of the segmented catheter 10 is an atraumatic tip 19 that possesses softness or even elastic properties as will be generally appreciated by those skilled in the art. A preferred material is a polyurethane such as Pellethane 80AE. Usually tip 19 includes radiopaque material for visibility during the procedure with the aid of X-ray fluoroscopy or other suitable imaging equipment.

With reference to FIG. 2, the longitudinal cross-section shown therein is of the distal end length of the guiding catheter 10. Shown intrinsically within the segment 17 is the braid 18. It will be noted that the polymer material has been molded over the braid. Also shown in FIG. 2 and in FIG. 3 is a liner 21 which preferably runs substantially the entire length of the guiding catheter. It is preferably constructed of a lubricious type material such as a polytetrafluoroethylene material or a Teflon polymer. Such provides a lubricious surface to facilitate insertion of the therapeutic catheter or other treatment device therethrough.

FIG. 4 illustrates use of the invention during a cardiac angioplasty or angiography procedure. The first segment 14 is routed from the femoral artery, up through the descending aorta 22, through the aortic arch 23 and into the heart 24. More specifically, the column-like first segment or handle extends from the insertion point at the femoral artery through the aorta to the aortic branch. This is a substantially straight segment of blood vessel which accommodates the stiff elongated proximal column tube. The second segment 15 is routed through the aortic arch, the interface 25 between the second segment 15 and the first or stiffest and longest segment or handle 14 being positioned at or near the beginning of the aortic arch. In an exemplary illustration, the interface 25 is located about 15 to about 30 cm proximal of the distal tip 19. The distalmost tube segment 17 will extend about 3 cm to about 8 cm from the distal tip. In this way, the second segment 15 is routed through the aortic arch, the catheter accommodating this shape by its greater flexibility. When provided, the intermediate tube segment 16 is routed very near the heart, requiring greater flexibility, and the fourth segment 17 is routed into the smaller coronary arteries, requiring the greatest flexibility.

EXAMPLE 1

Figure 6:
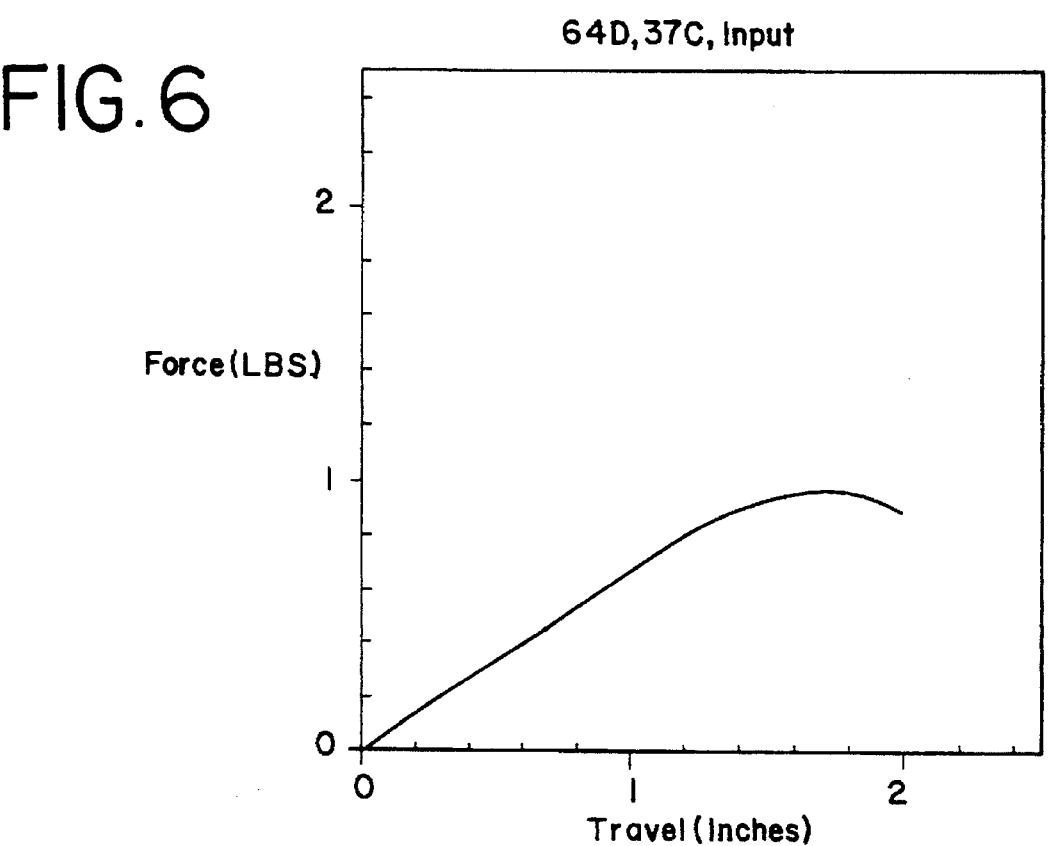
FIG. 6 is a plot as in FIG. 5, except it is for a proximalmost elongated guiding catheter tube having a stiffness less than that of the tube which is the subject of FIG. 5.

FIGS. 5 and 6 illustrate longitudinal load bending tests for elongated proximal column tubes made of two different types of polymers. Catheter tubings of a size suitable for use in making the elongated proximal column tube 14 were tested at typical body temperature, 37° C. A constant force was exerted on the proximal end of each tube, and the reaction force which was measured with a gauge sensor is reported and is plotted against the travel of the catheter tube. A comparison of FIG. 5, which reports these data for catheter tubing made of 75 D Nylon 12, with FIG. 6, which reports these data for 64 D Nylon 12, shows that the 75 D material holds its shape under these elevated temperature conditions more so than does the 64 D material. This illustrates the improved longitudinal stiffness or column strength of the 75 D catheter length when compared with the 64 D catheter length. This also illustrates the improved responsiveness and handling quickness of the 75 D material from the point of view of longitudinal or axial stresses.

EXAMPLE 2

Lateral stiffness testing was carried out. Two types of catheter tubings as generally discussed in connection with Example 1 were clamped at one end. Force was applied at the other end in generally cantilevered fashion. The force was increased until kinking occurred. The maximum force required to kinking was noted. In the case of the 75 D tubing, the maximum force indicating lateral stiffness was 242 gm-cm$^2$, while the maximum force for the 64 D tube was 183 gm-cm$^2$. In addition, the kink angle measured for the 75 D tube was 32°, while that for the 64 D tube was 45°. The conclusion is reached that the 75 D elongated proximal column tube or handle 14 of the invention is improved over a more conventional guiding catheter tube material such as that having a hardness of 64 D in that more force is required to bend the column tube 14 and same does not bend as much or kink as much when subjected to lateral forces.

EXAMPLE 3

Tubes as tested in Examples 1 and 2 were subjected to torque testing. One end of the tube was clamped, while the other end was attached to a motorized device for exerting radial or twisting forces onto the tube. The torque required to kink the tube was measured. In the case of the 75 D tube, the 75 D tube withstood a torque of 59.368N-mm, the movement being through a radial angle of 8.13N-mm per radian. For the 64 D tube, the torque required for initial twisting was 42.294 N-mm, the amount of twisting being 8.268N-mm per radian. This illustrates the improved torque resistance of the elongated proximal column tube 14 of the present invention when compared with more conventional 64 D guiding catheter tubes. This, as well as the other tests reported herein, illustrate the improved one-to-one responsiveness, both in terms of movement and time.

It will be understood that the embodiments of the present invention which have been described are illustrative of some of the applications of the principles of the present invention. Numerous modifications may be made by those skilled in the art without departing from the true spirit and scope of the invention.

We claim:

1. A guiding catheter having enhanced control characteristics and a distal portion adapted to be shaped into a curved configuration for use within a body vessel, the guiding catheter comprising:

an elongated catheter tube assembly, said tube assembly having a proximal end portion, a distal end portion having a tip member, and a lumen extending between said proximal and said distal end portions;

a hub connected to said proximal end portion of the tube assembly;

said elongated catheter tube assembly including an elongated proximal column tube extending from said proximal end portion to a proximalmost interface location along said elongated catheter tube assembly, said elongated proximal column tube having a stiffness ranging between Shore 70 D and about Shore 80 D;

said elongated catheter tube assembly including a modulated-stiffness tube assembly extending from said proximalmost interface location to said tip member, said modulated-stiffness tube assembly having a plurality of tube sections each of which has different stiffness properties such that these tube sections are of decreasing stiffness in the distal direction;

said elongated proximal column tube has a length substantially greater than and has a stiffness significantly greater than the total length and the maximum stiffness, respectively, of said modulated-stiffness tube assembly and of each individual section of the modulated-stiffness tube assembly;

said modulated-stiffness tube assembly has a proximalmost tube section, a distalmost tube section, and an intermediate tube section;

said proximalmost one of said tube sections of the modulated-stiffness tube assembly has a stiffness ranging between about 58 D and 70 D and always less than said stiffness of the elongated proximal column tube;

said proximalmost tube section is nylon homopolymer, said distalmost tube section is nylon copolymer, and said intermediate tube section is a polymer which is a blend of nylon homopolymer and nylon copolymer; and wherein said nylon homopolymer has a stiffness of between about Shore 58 D and about Shore 70 D, and wherein said nylon copolymer has a stiffness of between about Shore 30 D and about Shore 50 D.

2. The guiding catheter according to claim 1, wherein said elongated proximal column tube has a nylon tube extending its length.

3. The guiding catheter according to claim 2, wherein said nylon is Nylon 12.

4. The guiding catheter according to claim 2, wherein said nylon is Nylon 12 homopolymer.

5. The guiding catheter according to claim 1, wherein said proximalmost interface location is an assembly location between said elongated proximal column tube and said modulated-stiffness tube assembly.

6. The guiding catheter according to claim 5, wherein said assembly location welds together respective end surfaces of said elongated proximal column tube and a proximalmost tube section of said modulated-stiffness tube assembly.

7. The guiding catheter according to claim 1, wherein said plurality of tube sections of the modulated-stiffness tube assembly are joined together at one or more assembly locations.

8. The guiding catheter according to claim 7, wherein said assembly locations weld together respective end surfaces of said tube sections of the modulated-stiffness tube assembly.

9. The guiding catheter according to claim 1, wherein said stiffness of the elongated proximal column tube is about Shore 75 D.

10. The guiding catheter according to claim 9, wherein said proximalmost one of said tube sections of the modulated-stiffness tube assembly has a stiffness of about Shore 64 D.

11. The guiding catheter according to claim 1, wherein said nylon homopolymer is Nylon 12.

12. The guiding catheter according to claim 1, wherein said stiffness of the nylon homopolymer is about Shore 64 D, and said stiffness of the nylon copolymer is about Shore 40 D.

13. The guiding catheter according to claim 1, further including a lubricious liner defining said lumen of said elongated catheter tube assembly along at least a major length thereof.

14. The guiding catheter according to claim 1, further including a braid within said elongated catheter tube assembly along at least a major length thereof.

15. The catheter according to claim 1, wherein said intermediate segment has a stiffness of between about 45 D and about 65 D, and said distalmost segment has a stiffness of between about 30 D and about Shore 50 D, and wherein said proximalmost segment stiffness is greater than that of said intermediate segment and said intermediate segment stiffness is greater than that of said distalmost segment.

16. A guiding catheter having enhanced control characteristics and a distal portion adapted to be shaped into a curved configuration for use within a body vessel, the guiding catheter comprising:

an elongated catheter tube assembly, said tube assembly having a proximal end portion, a distal end portion having a tip member, and a lumen extending between said proximal and said distal end portions;

a hub connected to said proximal end portion of the tube assembly;

said elongated catheter tube assembly including an elongated proximal column tube extending from said proximal end portion to a proximalmost interface location along said elongated catheter tube assembly, said elongated proximal column tube having a stiffness ranging between Shore 70 D and about Shore 80 D;

said elongated catheter tube assembly including a modulated-stiffness tube assembly extending from said proximalmost interface location to said tip member, said modulated-stiffness tube assembly having a plurality of tube sections each of which has different stiffness properties such that these tube sections are of decreasing stiffness in the distal direction;

said elongated proximal column tube has a length substantially greater than and has a stiffness significantly greater than the total length and the maximum stiffness, respectively of said modulated-stiffness tube assembly and of each individual section of the modulated-stiffness tube assembly;

a proximalmost one of said tube sections of the modulated-stiffness tube assembly has a stiffness of about Shore 64 D;

said proximalmost tube section is nylon homopolymer, a distalmost tube section of the modulated-stiffness tube assembly is nylon copolymer, and an intermediate tube section of the modulated-stiffness tube assembly is a polymer which is a blend of nylon homopolymer and nylon copolymer.

\* \* \* \* \*